United States Patent
Hamann et al.

(10) Patent No.: US 10,328,264 B2
(45) Date of Patent: Jun. 25, 2019

(54) METHOD AND APPARATUS FOR NEUROSTIMULATION WITH PREVENTION OF NEURAL ACCOMMODATION

(71) Applicant: Cardiac Pacemakers, Inc., St. Paul, MN (US)

(72) Inventors: Jason J. Hamann, Blaine, MN (US); David J. Ternes, Roseville, MN (US); Stephen B. Ruble, Lino Lakes, MN (US); Juan Gabriel Hincapie Ordonez, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 15/658,139

(22) Filed: Jul. 24, 2017

(65) Prior Publication Data

US 2018/0050207 A1    Feb. 22, 2018

Related U.S. Application Data

(63) Continuation of application No. 13/472,988, filed on May 16, 2012, now abandoned.
(Continued)

(51) Int. Cl.
*A61N 1/36* (2006.01)

(52) U.S. Cl.
CPC ..... *A61N 1/36135* (2013.01); *A61N 1/36167* (2013.01); *A61N 1/36053* (2013.01); *A61N 1/36114* (2013.01)

(58) Field of Classification Search
CPC ............ A61N 1/36135; A61N 1/36167; A61N 1/36053; A61N 1/36114
See application file for complete search history.

(56) References Cited

U.S. PATENT DOCUMENTS

| | | | |
|---|---|---|---|
| 4,541,432 | A | 9/1985 | Molina-Negro et al. |
| 4,759,368 | A | 7/1988 | Spanton et al. |

(Continued)

FOREIGN PATENT DOCUMENTS

| | | |
|---|---|---|
| JP | 2009513248 A | 4/2009 |
| JP | 2011050627 A | 3/2011 |

(Continued)

OTHER PUBLICATIONS

"U.S. Appl. No. 13/472,988, Advisory Action dated Jun. 2, 2014", 8 pgs.
(Continued)

*Primary Examiner* — Catherine M Voorhees
(74) *Attorney, Agent, or Firm* — Schwegman Lundberg & Woessner, P.A.

(57) ABSTRACT

A neurostimulation system delivers neurostimulation to a patient using one or more primary parameters and one or more secondary parameters. The one or more primary parameters are controlled for maintaining efficacy of the neurostimulation. The one or more secondary parameters are adjusted for preventing the patient from developing neural accommodation. In various embodiments, values for the one or more secondary parameters are varied during the delivery of the neurostimulation for prevention of neural accommodation that may result from a constant or periodic pattern of stimulation pulses.

20 Claims, 10 Drawing Sheets

Related U.S. Application Data

(60) Provisional application No. 61/486,573, filed on May 16, 2011.

(56) References Cited

U.S. PATENT DOCUMENTS

| | | | |
|---|---|---|---|
| 4,938,223 | A | 7/1990 | Charters et al. |
| 5,512,057 | A | 4/1996 | Reiss et al. |
| 5,683,422 | A | 11/1997 | Rise |
| 7,174,213 | B2 * | 2/2007 | Pless .................. A61N 1/36064 607/45 |
| 7,801,601 | B2 | 9/2010 | Maschino et al. |
| 7,831,305 | B2 | 11/2010 | Gliner |
| 2003/0135248 | A1 * | 7/2003 | Stypulkowski .... A61N 1/36071 607/73 |
| 2006/0069415 | A1 | 3/2006 | Cameron et al. |
| 2006/0079945 | A1 | 4/2006 | Libbus |
| 2007/0073356 | A1 | 3/2007 | Rooney et al. |
| 2007/0073357 | A1 | 3/2007 | Rooney et al. |
| 2007/0150034 | A1 | 6/2007 | Rooney et al. |
| 2008/0243204 | A1 | 10/2008 | Uthman et al. |
| 2009/0076561 | A1 | 3/2009 | Libbus et al. |
| 2010/0023090 | A1 | 1/2010 | Jaax et al. |
| 2011/0009919 | A1 | 1/2011 | Carbunaru et al. |
| 2011/0106197 | A1 | 5/2011 | Arcot-Krishnamurthy et al. |
| 2011/0257708 | A1 * | 10/2011 | Kramer ................ A61N 1/0551 607/62 |
| 2012/0095530 | A1 | 4/2012 | Chavan et al. |
| 2012/0296395 | A1 | 11/2012 | Hamann et al. |

FOREIGN PATENT DOCUMENTS

| | | | |
|---|---|---|---|
| JP | 2014516692 A | 7/2014 | |
| WO | WO 2005115536 A1 * | 12/2005 | ......... A61N 1/36021 |
| WO | WO-2012158766 A1 | 11/2012 | |

OTHER PUBLICATIONS

"U.S. Appl. No. 13/472,988, Appeal Brief filed Aug. 26, 2014", 15 pgs.

"U.S. Appl. No. 13/472,988, Appeal Decision dated May 23, 2017", 15 pgs.

"U.S. Appl. No. 13/472,988, Final Office Action dated Apr. 3, 2014", 17 pgs.

"U.S. Appl. No. 13/472,988, Non Final Office Action dated Nov. 14, 2013", 16 pgs.

"U.S. Appl. No. 13/472,988, Response filed Feb. 13, 2014 to Non Final Office Action dated Nov. 14, 2013", 13 pgs.

"U.S. Appl. No. 13/472,988, Response filed May 23, 2014 to Final Office Action dated Apr. 3, 2014", 12 pgs.

"International Application Serial No. PCT/US2012/038094, International Preliminary Report on Patentability dated Nov. 28, 2013", 9 pgs.

"International Application Serial No. PCT/US2012/038094, International Search Report dated Jul. 24, 2012", 6 pgs.

"International Application Serial No. PCT/US2012/038094, Written Opinion dated Jul. 24, 2012", 8 pgs.

* cited by examiner

METHOD AND APPARATUS FOR NEUROSTIMULATION WITH PREVENTION OF NEURAL ACCOMMODATION

CLAIM OF PRIORITY

This application is a continuation of U.S. application Ser. No. 13/472,988, filed May 16, 2012, which claims the benefit of priority under 35 U.S.C. § 119(e) of Hamann et al., U.S. Provisional Patent Application Ser. No. 61/486,573, entitled "METHOD AND APPARATUS FOR NEUROSTIMULATION WITH PREVENTION OF NEURAL ACCOMMODATION", filed on May 16, 2011, each of which is herein incorporated by reference in its entirety.

TECHNICAL FIELD

This document relates generally to neurostimulation and more particularly to a neurostimulation system that varies stimulation parameters to prevent neural accommodation while maintaining effectiveness of neurostimulation.

BACKGROUND

Neurostimulation has been applied to modulate various physiologic functions and treat various diseases. For example, cardiovascular functions are modulated by neural signals in portions of the autonomic nervous system. The heart is innervated with sympathetic and parasympathetic nerves. Neural activities in these nerves are known to regulate, among other things, heart rate, blood pressure, and myocardial contractility. Modulation of such neural activities by neurostimulation therefore provides for modulation of such cardiovascular functions. One example is the modulation of cardiac functions in a patient suffering heart failure or myocardial infarction. Electrical stimulation applied to the vagus nerve is known to decrease the heart rate and the contractility, lengthening the systolic phase of a cardiac cycle, and shortening the diastolic phase of the cardiac cycle. Such effects of vagus nerve stimulation allow for control of myocardial remodeling. In addition to treating cardiac disorders such as myocardial remodeling, vagus nerve stimulation is also known to be effective in treating disorders including, but not limited to, depression, anorexia nervosa/eating disorders, pancreatic function, epilepsy, hypertension, inflammatory disease, and diabetes.

However, neurostimulation may decrease its effectiveness in a patient after it has been applied to the patient for a period of time. Such neural accommodation or tolerance may be due to neural reorganization (plasticity) or attenuation of end organ responsiveness. Neural plasticity is the change of structure, function, and organization of neurons in response to new experience. An end organ may decrease its responsiveness to stimulation due to receptor down regulation, reduced sensitivity of receptors, change in second messenger systems, cell signaling cascades, etc. Thus, there is a need for maintaining efficacy of neurostimulation over time, especially when the neurostimulation is applied as a long-term therapy.

SUMMARY

A neurostimulation system delivers neurostimulation to a patient using one or more primary parameters and one or more secondary parameters. The one or more primary parameters are controlled for maintaining efficacy of the neurostimulation. The one or more secondary parameters are adjusted for preventing the patient from developing neural accommodation. In various embodiments, values for the one or more secondary parameters are varied during the delivery of the neurostimulation for prevention of neural accommodation that may result from a constant or periodic pattern of stimulation pulses.

In one embodiment, an implantable medical device includes a stimulation output circuit, a storage device, a control circuit, and an implantable housing encapsulating the stimulation output circuit, the storage device, and the control circuit. The stimulation output circuit delivers neurostimulation during therapy sessions. The storage device stores values of a plurality of stimulation parameters including one or more primary parameters and one or more secondary parameters. The one or more primary parameters each have a value selected for efficacy of the neurostimulation. The one or more secondary parameters each have a value adjustable for preventing neural accommodation while maintaining the efficacy of the neurostimulation. The values include a plurality of value sets for the one or more secondary parameters. The value sets are each a set of one or more values each given to one of the one or more secondary parameters. The control circuit controls the delivery of the neurostimulation using the plurality of stimulation parameters. The control circuit includes a parameter adjuster that adjusts one or more parameters of the plurality of parameters. The parameter adjuster includes a secondary parameter adjuster that selects a subset of one or more value sets from the stored plurality of value sets for the one or more secondary parameters for each session of the therapy sessions such that the one or more secondary parameters are adjusted randomly through the therapy sessions.

In one embodiment, a method for operating an implantable medical device is provided. Values of a plurality of stimulation parameters are received and stored. The plurality of stimulation parameters includes one or more primary parameters and one or more secondary parameters. The one or more primary parameters each have a value selected for efficacy of neurostimulation. The one or more secondary parameters each have a value adjustable for preventing neural accommodation while maintaining the efficacy of the neurostimulation. The values include a plurality of value sets for the one or more secondary parameters. The value sets are each a set of one or more values each given to one of the one or more secondary parameters. Neurostimulation is delivered during therapy sessions, and the delivery is controlled using the plurality of stimulation parameters. This includes selecting a subset of one or more value sets from the stored plurality of value sets for the one or more secondary parameters for each session of the therapy sessions and adjusting the one or more secondary parameters during the therapy sessions. The subset is selected to allow for adjusting the one or more secondary parameters randomly through the therapy sessions.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their legal equivalents.

References to "an", "one", or "various" embodiments in this disclosure are not necessarily to the same embodiment, and such references contemplate more than one embodiment.

This document discusses a system and method for delivering neurostimulation to a patient and controlling stimulation parameters to prevent the effectiveness of the neurostimulation from being substantially attenuated by neural accommodation. Neural accommodation tends to develop in response to neurostimulation with a constant or periodic stimulus pattern, such as substantially identical electrical stimulation pulses delivered continuously or periodically at a substantially constant pulse frequency and substantially constant duty cycle. The present system avoids such a constant or periodic pattern by varying values of one or more stimulation parameters during the delivery of the neurostimulation while maintaining the effectiveness of the neurostimulation by controlling one or more other parameters.

For the purpose of the present subject matter as discussed in this document, "prevention" of neural accommodation includes attempts to avoid or attenuate neural accommodation before it is detected by avoiding a constant or periodic pattern of stimulation pulses and, if neural accommodation occurs, abating neural accommodation after it is detected. In various embodiments, such prevention may be applied at any time during a neurostimulation therapy, when there is a concern of therapy efficacy being compromised by neural accommodation.

Figure 1:
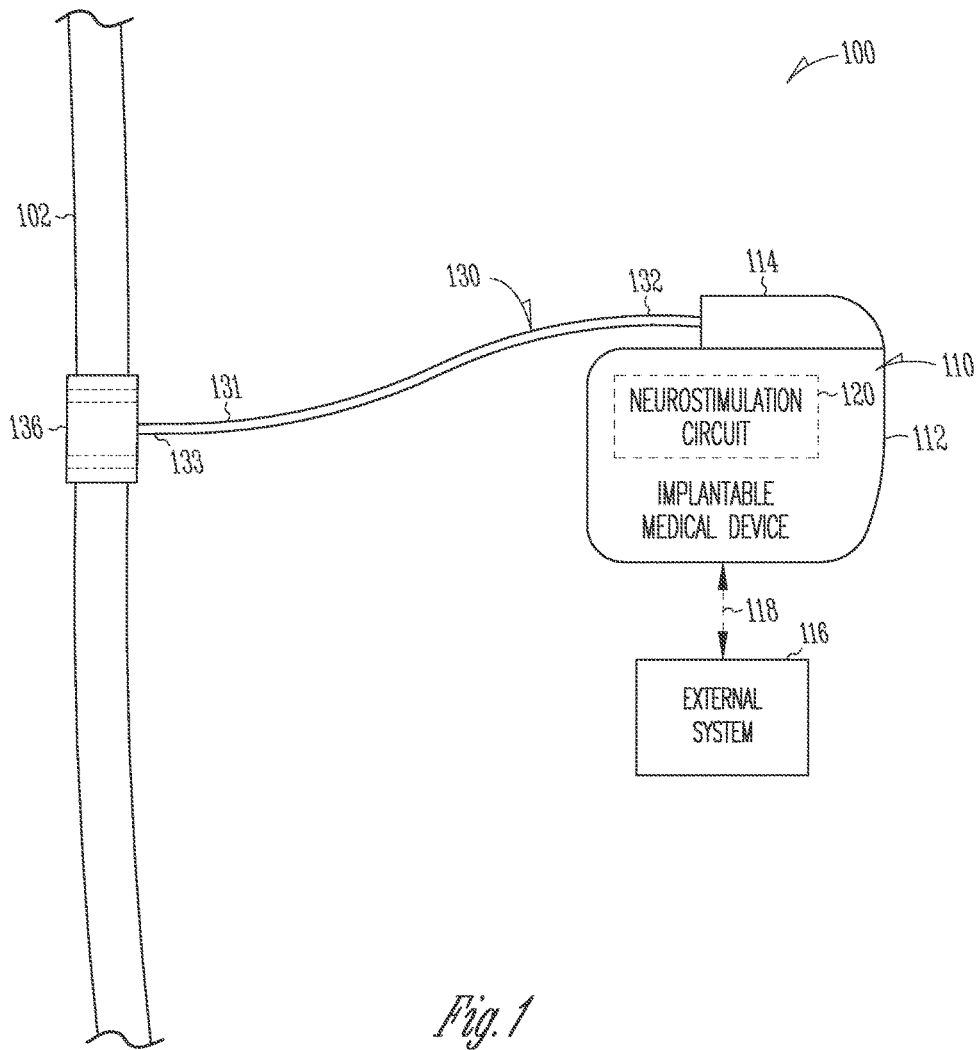
FIG. 1 is an illustration of an embodiment of a neurostimulation system and portions of an environment in which the system is used.

FIG. 1 is an illustration of an embodiment of a neurostimulation system 100 and portions of an environment in which system 100 is used. FIG. 1 shows a portion of a nerve 102 and a stimulation electrode 136 placed on nerve 102 to allow for delivery of neurostimulation to nerve 102. In various embodiments, stimulation electrode 136 may be placed on nerve 102 or in a location suitable for delivering the neurostimulation to nerve 102. In one embodiment, nerve 102 represents a portion of the autonomic nervous system, such as the vagus nerve and the carotid sinus nerve. In another embodiment, nerve 102 represents a portion of the spinal cord or the spinal nerves. A neurostimulation therapy is applied by delivering controlled stimulation to nerve 102 to modulate one or more physiological functions controlled by nerve 102. In various embodiments, system 100 is used to treat abnormal conditions such as heart failure with low ejection fraction, heart failure with moderate ejection fraction, post-myocardial infarction, refractory hypertension, angina, arrhythmia, apnea, diabetes, and inflammation. In various embodiments, system 100 is used to deliver neurostimulation to any nerve in a patient to modulate a physiological function of the patient while preventing the patient from developing neural accommodation.

In the illustrated embodiment, system 100 includes an implantable medical device 110 electrically coupled to electrode 136 through an implantable lead 130. Implantable medical device 110 includes a neurostimulation circuit 120 encapsulated in an implantable housing 112, and a header 114 attached to implantable housing 112 and providing for connection between neurostimulation circuit 120 and lead 130. In one embodiment, implantable medical device 110 is a neurostimulator. In other embodiments, in addition to a neurostimulator including neurostimulation circuit 120, implantable medical device 110 includes one or more of a cardiac pacemaker, a cardioverter/defibrillator, a drug delivery device, a biologic therapy device, and any other monitoring or therapeutic devices. These devices may interact with each other. For example, neural activities may be sensed by neurostimulation circuit 120 to indicate a need for cardiac stimulation and/or to control the timing of pacing pulse deliveries from the cardiac pacemaker. Likewise, cardiac activities are sensed by the cardiac pacemaker to control the timing of neural stimulation pulse deliveries from neurostimulation circuit 120, such as to synchronize neural stimulation to cardiac cycles or respiratory cycles. Lead 130 includes a proximal end 132, a distal end 133, and an elongate body 131 coupled between proximal end 132 and distal end 133. Proximal end 132 is configured to be connected to implantable medical device 110. Distal end 133 includes, or is otherwise coupled to, stimulation electrode 136. In various other embodiments, stimulation electrode 136 includes any form of electrode that allows for activation of nerve 102 by electrical stimulation delivered from neurostimulation circuit 120.

Neurostimulation circuit 120 delivers neurostimulation to nerve 102 through lead 130 and controls the delivery of the neurostimulation using a plurality of stimulation parameters. The plurality of stimulation parameters includes one or more parameters each having a value adjustable for preventing neural accommodation while maintaining efficacy of the neurostimulation. Examples of such one or more parameters when the neurostimulation is delivered as electrical pulses include length of the on-portion of the duty cycle, length of the off-portion of the duty cycle, pulse amplitude, pulse width, frequency, pulse waveform, and envelop of the on-portion of the duty cycle (amplitude, width, etc.). Various embodiments of neurostimulation circuit 120 are discussed below with reference to FIGS. 2 and 3.

System 100 also includes an external system 116, which communicates with implantable medical device 110 via a telemetry link 118. External system 116 allows a user such as a physician or other caregiver or the patient to control operation of implantable medical device 110 and monitor the status of the patient and/or implantable medical device 110.

Figure 2:
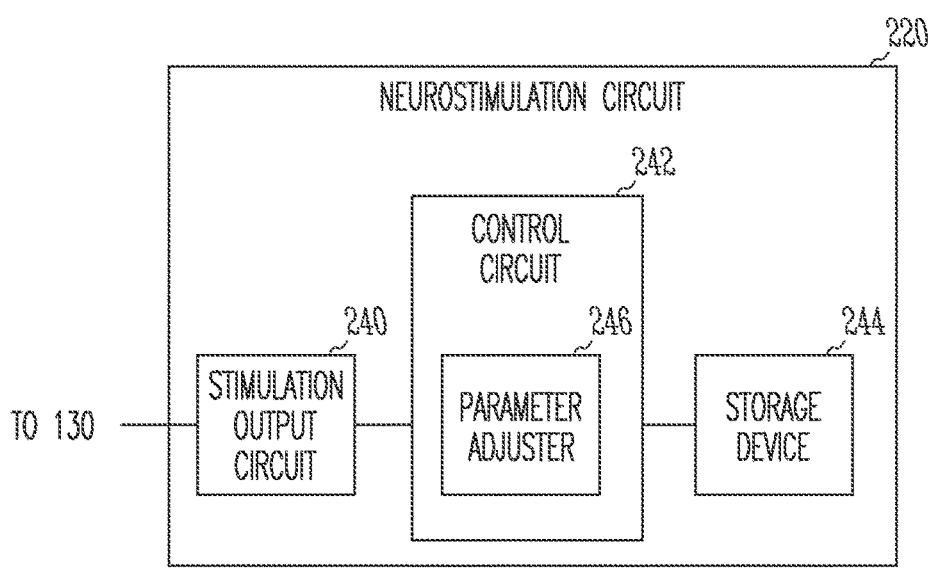
FIG. 2 is a block diagram illustrating an embodiment of a neurostimulation circuit.

FIG. 2 is a block diagram illustrating an embodiment of a neurostimulation circuit 220. Neurostimulation circuit 220 represents an embodiment of neurostimulation circuit 120 and includes a stimulation output circuit 240, a control circuit 242, and a storage device 244. Stimulation output circuit 240 delivers neurostimulation to the patient during therapy sessions. In one embodiment, the delivery of the neurostimulation includes delivery of electrical pulses. Storage device 244 stores values of a plurality of stimulation parameters including one or more primary parameters and one or more secondary parameters. The one or more primary parameters each have a value selected for maintaining efficacy of the neurostimulation. The one or more secondary parameters each have a value adjustable for preventing neural accommodation without substantially compromising the efficacy of the neurostimulation. The stored values of the plurality of stimulation parameters include a plurality of value sets for the one or more secondary parameters. The value sets are each a set of one or more values each given to one of the one or more secondary parameters. Control circuit 242 controls the delivery of the neurostimulation using the plurality of stimulation parameters and includes a parameter adjuster 246. Parameter adjuster 246 adjusts one or more parameters of the plurality of parameters. In various embodiments, parameter adjuster 246 selects a different subset of one or more value sets from the stored plurality of value sets for the one or more secondary parameters for each session of the therapy sessions. The selection is performed according to various rules determined to prevent the patient from developing neural accommodation in response to the delivery of the neurostimulation.

In one embodiment, parameter adjuster 246 selects a subset of one or more value sets from the stored plurality of value sets for the one or more secondary parameters for each session of the therapy sessions such that the one or more secondary parameters are adjusted randomly or pseudo-randomly through the therapy sessions. This may be achieved by storing the value sets for the one or more secondary parameters in a randomized or pseudo-randomized order in storage device 244, or by configuring parameter adjuster 246 to randomly or pseudo-randomly select value sets from the plurality of value sets for the one or more secondary parameters stored in storage device 244. For various embodiments, pseudo-randomness refers to, for example, an order of values that is not truly randomized but arranged in a way approximating randomness by its potential effect in prevention of neural accommodation. In various embodiments as discussed in this document, randomness may include true randomness or pseudo-randomness.

In various embodiments, the one or more primary parameters are each a parameter whose value is determined and/or adjusted for efficacy. In one embodiment, each parameter of the one or more primary parameters is given a predetermined value. In one embodiment, parameter adjuster 246 adjusts each parameter of the one or more primary parameters as needed to maintain efficacy of the neurostimulation. One example of the one or more primary parameters includes one or more parameters being a measure of a total dose of the neurostimulation applied over a therapy session.

In various embodiments, the one or more secondary parameters are each a parameter whose value can be substantially adjusted without substantially affecting the efficacy of the neurostimulation. The value sets of the one or more secondary parameters are each determined to maintain efficacy of the neurostimulation and are substantially different from each other. One example of the one or more secondary parameters includes pulse amplitude and pulse width. The value sets each include a pulse amplitude value and a pulse width value selected based on a predetermined strength-duration curve.

In various embodiments, the circuit of system 100, including its various elements discussed in this document, is implemented using a combination of hardware and software (including firmware). In various embodiments, control circuit 242, including their various elements discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 3:
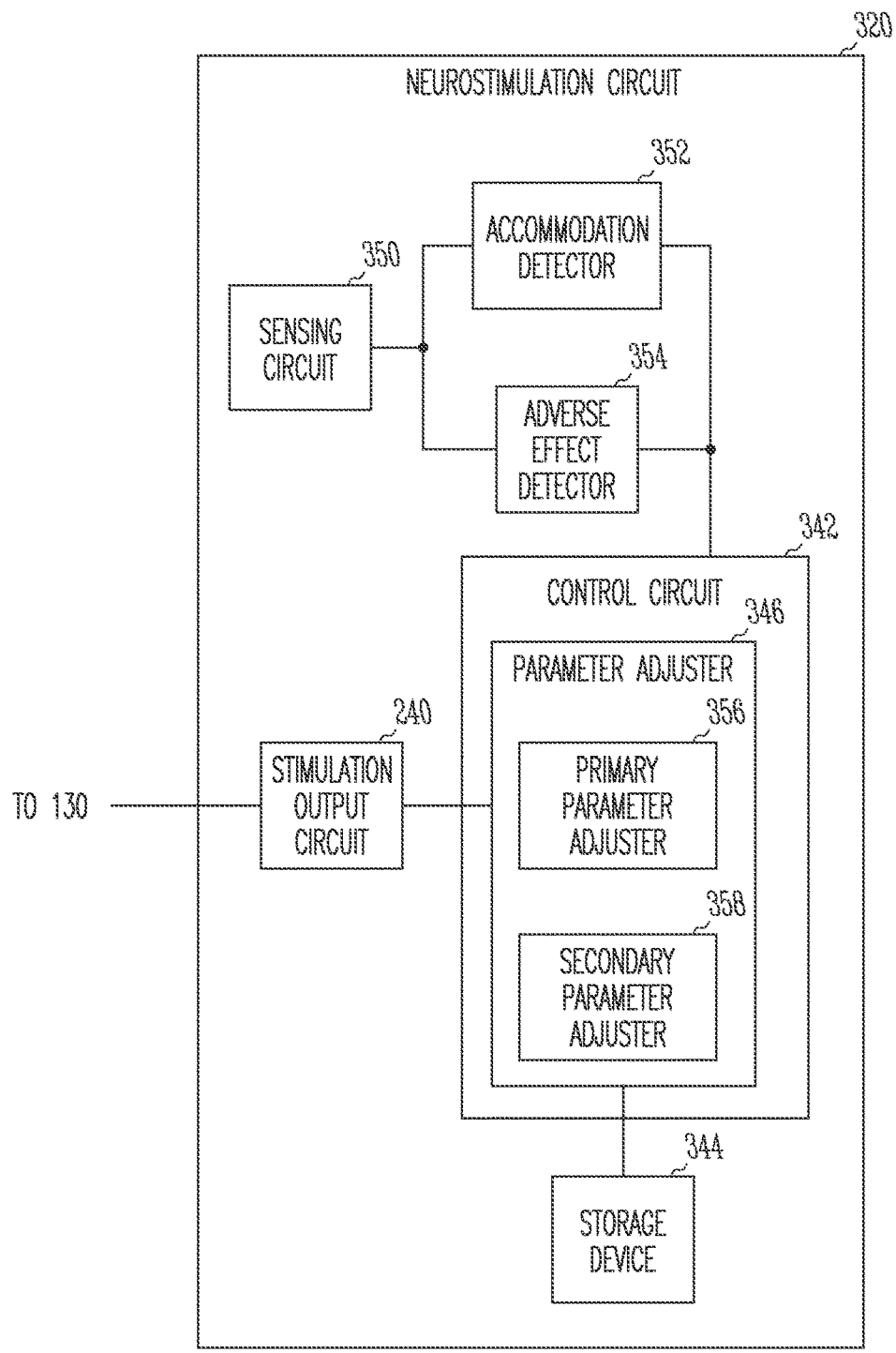
FIG. 3 is a block diagram illustrating another embodiment of the neurostimulation circuit.

FIG. 3 is a block diagram illustrating an embodiment of a neurostimulation circuit 320. Neurostimulation circuit 320 represents another embodiment of neurostimulation circuit 120 and includes stimulation output circuit 240, a sensing circuit 350, an accommodation detector 352, an adverse effect detector 354, a control circuit 342, and a storage device 344.

Sensing circuit 350 senses one or more physiological signals indicative of one or more effects of the delivery of the neurostimulation from stimulation output circuit 240. In one embodiment, at least one of the one or more physiological signals is indicative of a degree of modulation of one or more physiological functions by the neurostimulation. Such modulation results from responses of one or more nerves to which the neurostimulation is applied, and the one or more nerves innervate or otherwise control the one or more organs.

Accommodation detector 352 detects an indication of neural accommodation using the one or more physiological signals. In one embodiment, the indication of neural accommodation includes a substantial decrease in the degree of modulation of the one or more physiological functions by the neurostimulation. In another embodiment, the indication of neural accommodation includes a substantial increase in stimulation threshold as a percentage or absolute value, where the stimulation threshold is the minimum intensity of the neurostimuation that results in a detectable modulation of the one or more physiological functions in response to the neurostimulation.

Adverse effect detector 354 detects an indication of an adverse effect of the neurostimulation using the one or more physiological signals. In various embodiments, the adverse effect is an unintended effect of the neurostimulation. In one embodiment, the adverse effect is an unintended effect of the neurostimulation that is considered to be harmful to the patient.

Storage device 344 represents an embodiment of storage device 244 and stores values of the plurality of stimulation parameters including the one or more primary parameters and the one or more secondary parameters. In one embodiment, the plurality of value sets for the one or more secondary parameters are stored in storage device 344 as one or more sequences of value sets for the one or more secondary parameters. The one or more sequences are each generated for a therapy session. In one embodiment, a plurality of such sequences is stored to be used for multiple therapy sessions. A therapy session includes a programmed period of time during which the patient is treated by continuous or intermittent delivery of the neurostimulation. An intermittent delivery of the neustimulation is programmed to include periods during which the neurostimulation is delivered and periods during which the neurostimulation is not delivered. In one embodiment, the therapy sessions are timed according to a programmed schedule, such as being started on a substantially periodic basis.

Control circuit 342 represents an embodiment of control circuit 242 and controls the delivery of the neurostimulation using the plurality of stimulation parameters. Control circuit 342 includes a parameter adjuster 346, which represents an embodiment of parameter adjuster 246 and adjusts one or more parameters of the plurality of stimulation parameters. Parameter adjuster 346 includes a primary parameter adjuster 356 and a secondary parameter adjuster 358.

Primary parameter adjuster 356 adjusts the one or more primary parameters. In one embodiment, primary parameter adjuster 356 sets the value of each of the one or more primary parameters to a predetermined value, such as a value received from the user through external system 116 and telemetry link 118. In one embodiment, primary parameter adjuster 356 adjusts the value of each of the one or more primary parameters using the one or more physiological signals, such as to maintain a specified degree of modulation of one or more physiological functions by the neurostimulation as indicated by the one or more physiological signals.

Secondary parameter adjuster 358 adjusts the one or more secondary parameters. In various embodiments, secondary parameter adjuster 358 selects for each therapy session a subset of one or more value sets from the plurality of value sets for the one or more secondary parameters stored in storage device 344. In one embodiment, secondary parameter adjuster 358 randomly selects each value set of the one or more value sets from the stored plurality of value sets for each therapy session. In another embodiment, secondary parameter adjuster 358 selects each value set of the one or more value sets by cycling through the plurality of value sets in a predetermined order, such as cycling through the plurality of value sets stored in storage device 344 as a circular list. Secondary parameter adjuster 358 adjusts the one or more secondary parameters using the selected one or more value sets for the therapy session. In one embodiment, secondary parameter adjuster 358 adjusts the one or more secondary parameters in response to a detection of the indication of the neural accommodation by accommodation detector 352. In one embodiment, secondary parameter adjuster 358 adjusts the one or more secondary parameters in response to a detection of the indication of the adverse effect of the neurostimulation by adverse effect detector 354. In one embodiment, secondary parameter adjuster 358 adjusts the one or more secondary parameters in response to an adjustment to the one or more primary parameters by primary parameter adjuster 356.

In various embodiments, secondary parameter adjuster 358 selects prior to each therapy session a value set from the plurality of value sets for the one or more secondary parameters stored in storage device 344, and sets the one or more secondary parameters to the selected value set for the entire therapy session. In one embodiment, secondary parameter adjuster 358 randomly selects prior to the therapy session the value set from the plurality of value sets stored in storage device 344. In another embodiment, secondary parameter adjuster 358 selects prior to the therapy session the value set by cycling through the plurality of value sets in a predetermined order, such as cycling through the plurality of value sets stored in storage device 344 as a circular list.

In various embodiments, secondary parameter adjuster 358 selects value sets from the plurality of value sets for the one or more secondary parameters stored in storage device 344, and generates a sequence of value sets for each therapy session. The sequence of value sets includes the selected value sets with timing specified for using each of the selected value sets during the therapy session. In one embodiment, secondary parameter adjuster 358 randomly selects the value sets from the plurality of value sets stored in storage device 344. In another embodiment, secondary parameter adjuster 358 selects the value set by cycling through the plurality of value sets in a predetermined order, such as cycling through the plurality of value sets stored in storage device 344 as a circular list. In another embodiment, secondary parameter adjuster 358 randomizes an order of the selected value sets in the sequence of value sets. Secondary parameter adjuster 358 dynamically adjusts the one or more secondary parameters according to the sequence of value sets during the therapy session.

In various embodiments, one or more predetermined sequences of value sets for the one or more secondary parameters are stored in storage device 344, and secondary parameter adjuster 358 selects a sequence from the stored one or more predetermined sequences. In one embodiment, secondary parameter adjuster 358 randomly selects the sequence from the stored plurality of sequences. In another embodiment, secondary parameter adjuster 358 selects the sequence by cycling through the plurality of sequences in a predetermined order, such as cycling through the plurality of sequences stored in storage device 344 as a circular list. Secondary parameter adjuster 358 dynamically adjusts the one or more secondary parameters using the selected sequence during the therapy session.

Figure 4:
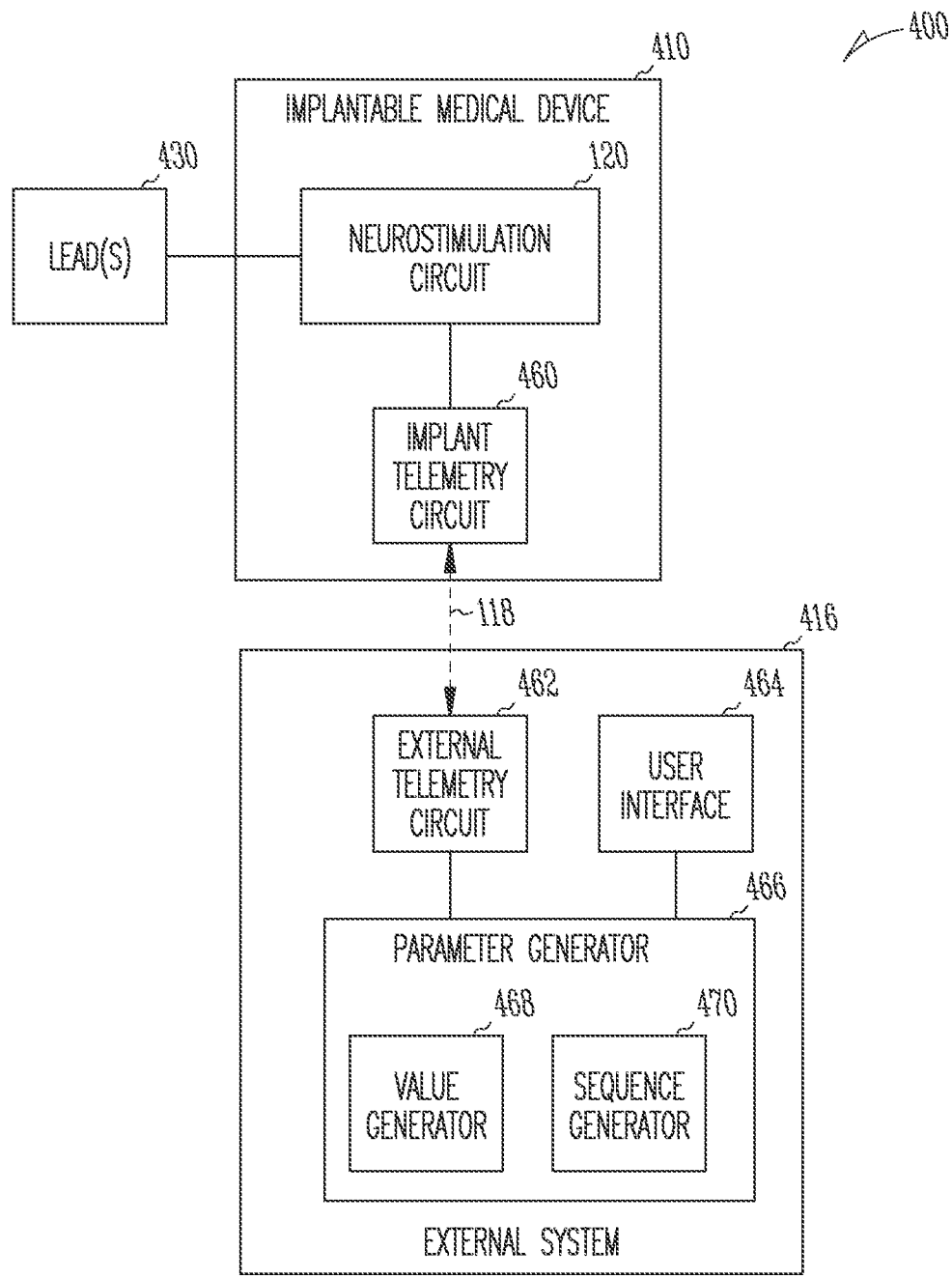
FIG. 4 is a block diagram illustrating an embodiment of the neurostimulation system.

FIG. 4 is a block diagram illustrating an embodiment of a neurostimulation system 400. System 400 represents an embodiment of system 100 and includes one or more leads 430, an implantable medical device 410, and an external system 416 communicating with implantable medical device 410 via telemetry link 118.

Lead(s) 430 provides therapy interface between system 400 and the patient receiving the neurostimulation therapy. In various embodiments, lead(s) 430 include any one or more leads suitable for delivering the neurostimulation to the patient, with lead 130 illustrating one example.

Implantable medical device 410 represents an embodiment of implantable medical device 110 and includes neurostimulation circuit 120 and an implant telemetry circuit 460. Implant telemetry circuit 460 allows implantable medical device 410 to communicate with external system 416 via telemetry link 118.

External system 416 represents an embodiment of external system 116 and includes an external telemetry circuit 462, a user interface 464, and a parameter generator 466. External telemetry circuit 462 allows external system 416 to communicate with implantable medical device 410 via telemetry link 118. User interface 464 allows the user to control operation of, and obtain information from, system 400. Parameter generator 466 generates values for the plurality of stimulation parameters, which are transmitted to implantable medical device 410 to be stored in storage device 244 or 344. In the illustrated embodiment, parameter generator 466 includes a value generator 468 and a sequence generator 470.

Value generator 468 generates the plurality of value sets for the one or more secondary parameters. In one embodiment, value generator 468 receives predetermined value sets from the user through user interface 464 or through a data interface. In another embodiment, value generator 468 generates the value sets according to predetermined criteria. For example, value generator 468 receives one or more values of the one or more primary parameters and generates the value sets using the received one or more values of the one or more primary parameters and the predetermined criteria. The predetermined criteria requires that the value sets each approximately maintain the one or more primary parameters at the received one or more values and including one or more values each within a specified value range for the one or more secondary parameters. In one embodiment, the values for each parameter of the one or more secondary parameters are given or generated in specified increments, and tested for the efficacy of the neurostimulation. In one embodiment, the efficacy of the neurostimulation is tested by sensing electromyogram (EMG) or accelerometer signals indicative of laryngeal response to the neurostimulation using different value sets for the one or more secondary parameters. In other embodiments, the efficacy of the neurostimulation is tested by monitoring one or more intended effects of the neurostimulation when the neurostimulation is delivered using different value sets for the one or more secondary parameters.

Sequence generator 470 generates the one or more sequences of value sets for the one or more secondary parameters to be stored in implantable medical device 410 when needed. In one embodiment, sequence generator 470 selects value sets from the value sets for the one or more secondary parameters generated from value generator 468, and determines an order for the selected value sets. In various embodiments, each of the one or more sequences of value sets for the one or more secondary parameters includes the selected value sets in a random order, a pseudo-random order, or other substantially aperiodic order (with no identical value sets repeating on a substantially periodic basis).

Figure 5:
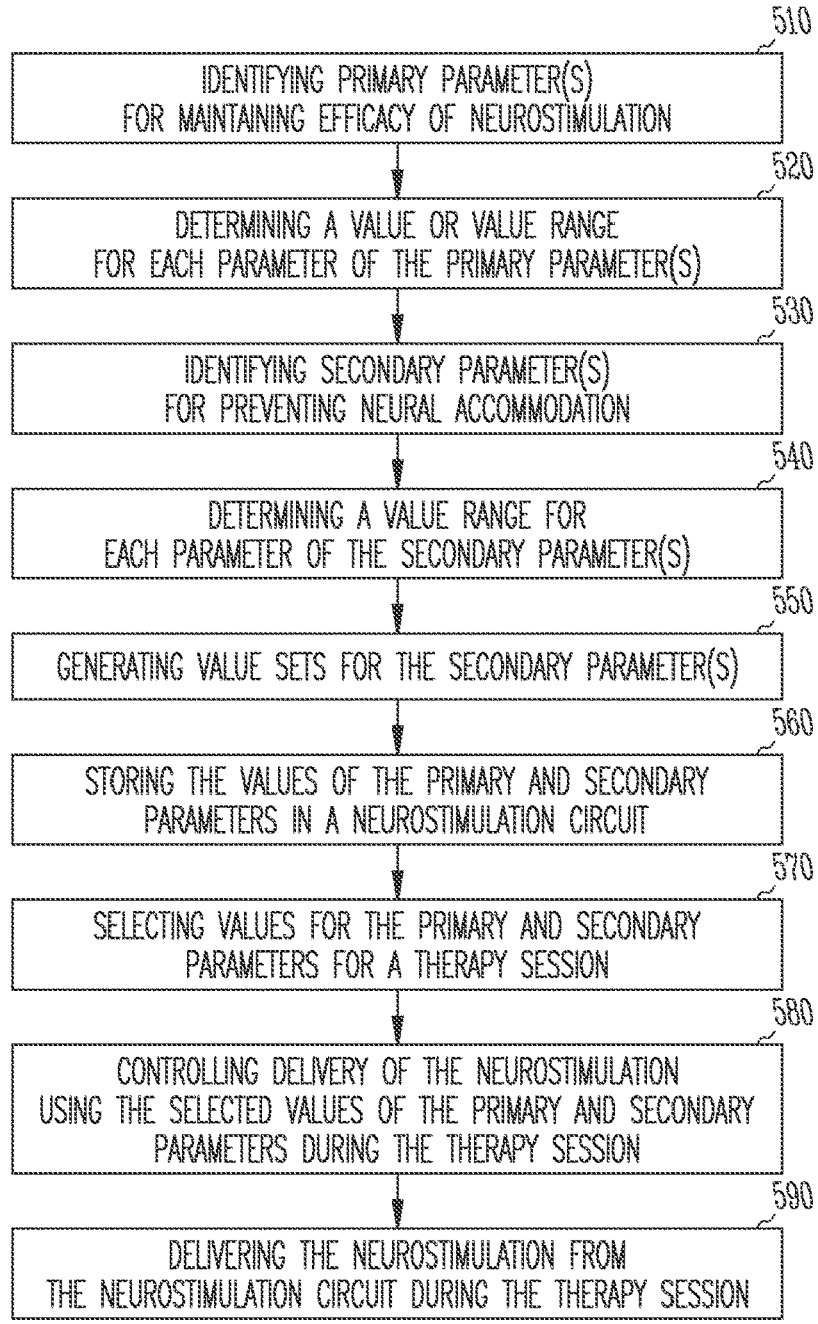
FIG. 5 is a flow chart illustrating an embodiment of a method for neurostimulation.

FIG. 5 is a flow chart illustrating an embodiment of a method 500 for neurostimulation. Method 500 provides for delivery of neurostimulation using a system such as system 100, including its various embodiments as discussed in this document, for prevention of neural accommodation while maintaining efficacy of the neurostimulation.

At 510, one or more primary parameters are identified for maintaining efficacy of the neurostimulation. At 520, a value or value range is determined for each parameter of the one or more primary parameters. The value or value range may be experimentally determined by monitoring the response of a patient to the delivery of the neurostimulation, and may be adjusted to maintain the efficacy of neurostimulation if necessary during or between therapy sessions.

At 530, one or more secondary parameters are identified for preventing neural accommodation without substantially affecting the efficacy of the neurostimulation. At 540, a value range is determined for each parameter of the one or more secondary parameters. The value range may be experimentally tested to verify that when the parameter varies within it, the efficacy of the neurostimulation is not substantially affected.

At 550, a plurality of value sets for the one or more secondary parameters is generated. The value sets each include a value for each parameter of the one or more secondary parameters, and are substantially different from each other. In one embodiment, one or more sequences of value sets are generated by selecting value sets from the plurality of value sets generated. At 560, the values of the one or more primary parameters and the one or more secondary parameters are stored in a neurostimulation circuit, such as neurostimulation circuit 120, including its various embodiments discussed in this document.

At 570, values for the one or more primary parameters and the one or more secondary parameters are selected by the neurostimulation circuit for a therapy session. In one embodiment, this includes selecting one or more value sets from the plurality of value sets for the one or more secondary parameters. In another embodiment, this includes selecting a sequence of value sets from the one or more sequences of value sets.

At 580, delivery of the neurostimulation is controlled using the selected values for the one or more primary parameters and the one or more secondary parameters during the therapy session. At 590, the neurostimulation is delivered from the neurostimulation circuit during the therapy session.

Figure 6:
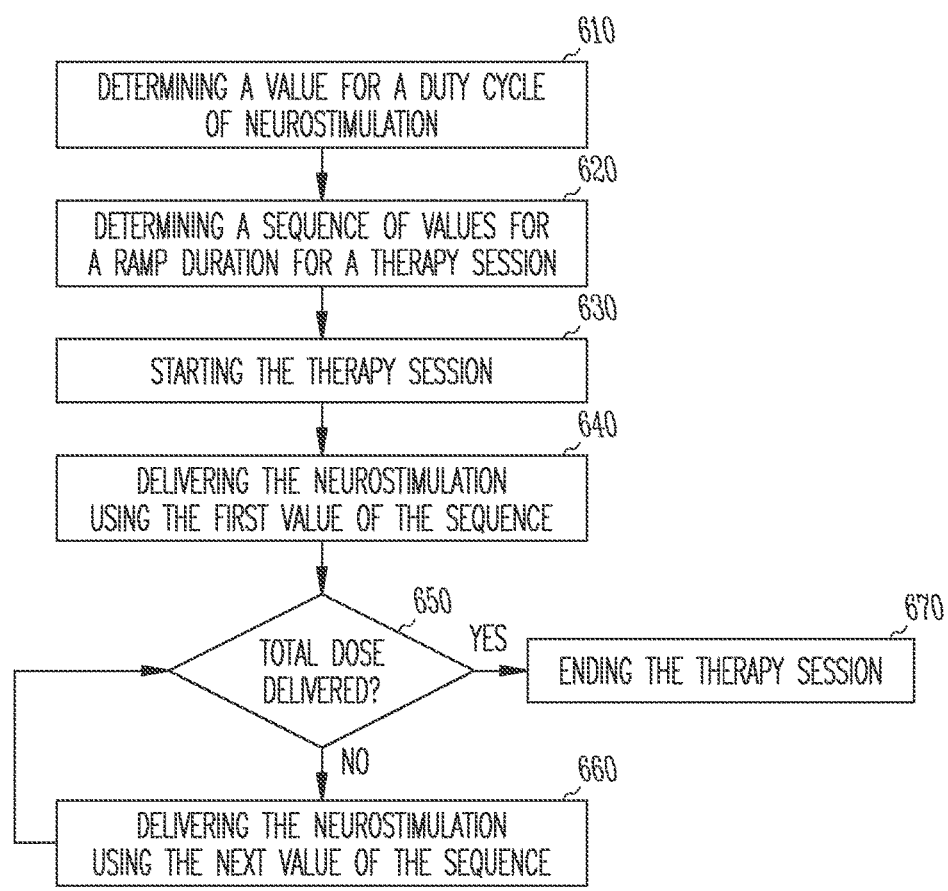
FIG. 6 is a flow chart illustrating an embodiment of a method for controlling neurostimulation for a specified duty cycle while preventing neural accommodation.

FIG. 6 is a flow chart illustrating an embodiment of a method 600 for controlling neurostimulation for a specified duty cycle while preventing neural accommodation. In one embodiment, method 600 is performed using system 100, including its various embodiments discussed in this document. In method 600, the neurostimulation is delivered at a specified duty cycle during therapy sessions. Each therapy session includes a plurality of total periods each being a sum of an on-period and an off-period. The on-period is a time period during which the neurostimulation is delivered. The off-period is a time period during which the neurostimulation is not delivered. The duty cycle is the ratio of the on-period to the total period and can be expressed in percentage. The duty cycle can also be expressed as a duty cycle ratio, which is a ratio of the on-period to the off-period. When the neurostimulation is delivered as electrical pulses with a specified duration of the therapy session and a specified pulse frequency, the duty cycle is a dosing parameter representative of the dose of the neurostimulation for the therapy session measured by the number of the electrical pulses delivered during the therapy session.

It is observed that when a ramp is introduced for the transition from the off-period to the on-period, and/or from the on-period to the off-period, within a limited range, the ramp duration does not substantially affect the efficacy of the neurostimulation. The ramp duration is a time interval during which the intensity of the neurostimulation gradually increases from zero to its value specified for the on-period, or a time interval during which the intensity of the neurostimulation gradually decreases to zero from its value specified for the on-period. In one embodiment, the ramp ends at the beginning of the on-period, or begins at the end of the on-period. Therefore, in method 600, the one or more primary parameters include the duty cycle (or equivalently, duty cycle ratio). The one or more secondary parameters include the ramp duration. In various embodiments, the intensity of the neurostimulation steps up or down in specified increments during the ramp duration.

At 610, a value for the duty cycle of the neurostimulation is determined for maintaining efficacy of the neurostimulation. At 620, a sequence of values for the ramp duration is determined for a therapy session. The values are within a limited range within which the ramp duration does not substantially affect the efficacy of the neurostimulation. In various embodiments, the sequence of values for the ramp duration includes the values arranged in a random order, a pseudo-random order, or other substantially aperiodic order. At 630, the therapy session is started. At 640, the neurostimulation is delivered using the first value of the sequence of values for the ramp duration. If the specified total dose of the neurostimulation has not been delivered at 650, the neurostimulation continues to be delivered using the next value in the sequence of values for the ramp duration at 660. If the specified total dose of the neurostimulation has been delivered at 650, the therapy session ends at 670.

Figure 7:
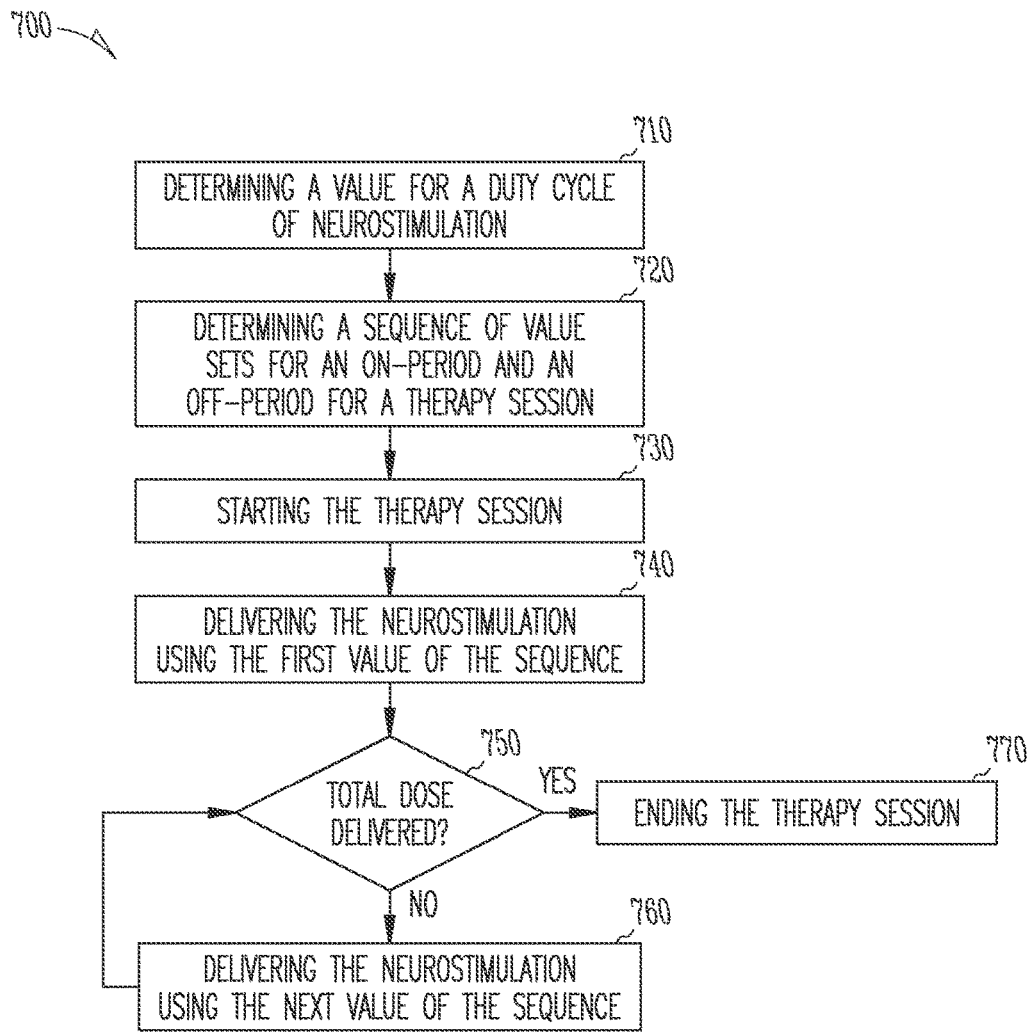
FIG. 7 is a flow chart illustrating another embodiment of a method for controlling neurostimulation for a specified duty cycle while preventing neural accommodation.

FIG. 7 is a flow chart illustrating an embodiment of a method 700 for controlling neurostimulation for a specified duty cycle while preventing neural accommodation. In one embodiment, method 700 is performed using system 100, including its various embodiments discussed in this document. In method 700, the neurostimulation is also delivered at a specified duty cycle during therapy sessions, with parameters including the total period, the on-period, the off-period, the duty cycle (or equivalently the duty cycle ratio), as discussed above for method 600.

It is observed that within a limited range, the value of the total period does not substantially affect the efficacy of the neurostimulation as long as the specified duty cycle is maintained. In other words, the values of the on-period and the off-period do not substantially affect the efficacy of the neurostimulation as long as the ratio of the on-period to the total period (the duty cycle) or the ratio of the on-period to the off-period (the duty cycle ratio) is maintained. Therefore, in method 700, the one or more primary parameters include the duty cycle (or equivalently, duty cycle ratio). The one or more secondary parameters include the on-period and the off-period (or equivalently, any two of the on-period, the off-period, and the total period).

At 710, a value for the duty cycle of the neurostimulation is determined for maintaining efficacy of the neurostimulation. At 720, a sequence of values sets for the on-period and the off-period is determined for a therapy session. The values are within a limited range within which the on-period and the off-period do not substantially affect the efficacy of the neurostimulation as long as the duty cycle is maintained. In various embodiments, the sequence of value sets for the on-period and the off-period includes the value sets arranged in a random order, a pseudo-random order, or other substantially aperiodic order. At 730, the therapy session is started. At 740, the neurostimulation is delivered using the first value of the sequence of value sets for the on-period and the off-period. If the specified total dose of the neurostimulation has not been delivered at 750, the neurostimulation continues to be delivered using the next value of the sequence of value sets for the on-period and the off-period at 760. If the specified total dose of the neurostimulation has been delivered at 750, the therapy session ends at 770.

Figure 8:
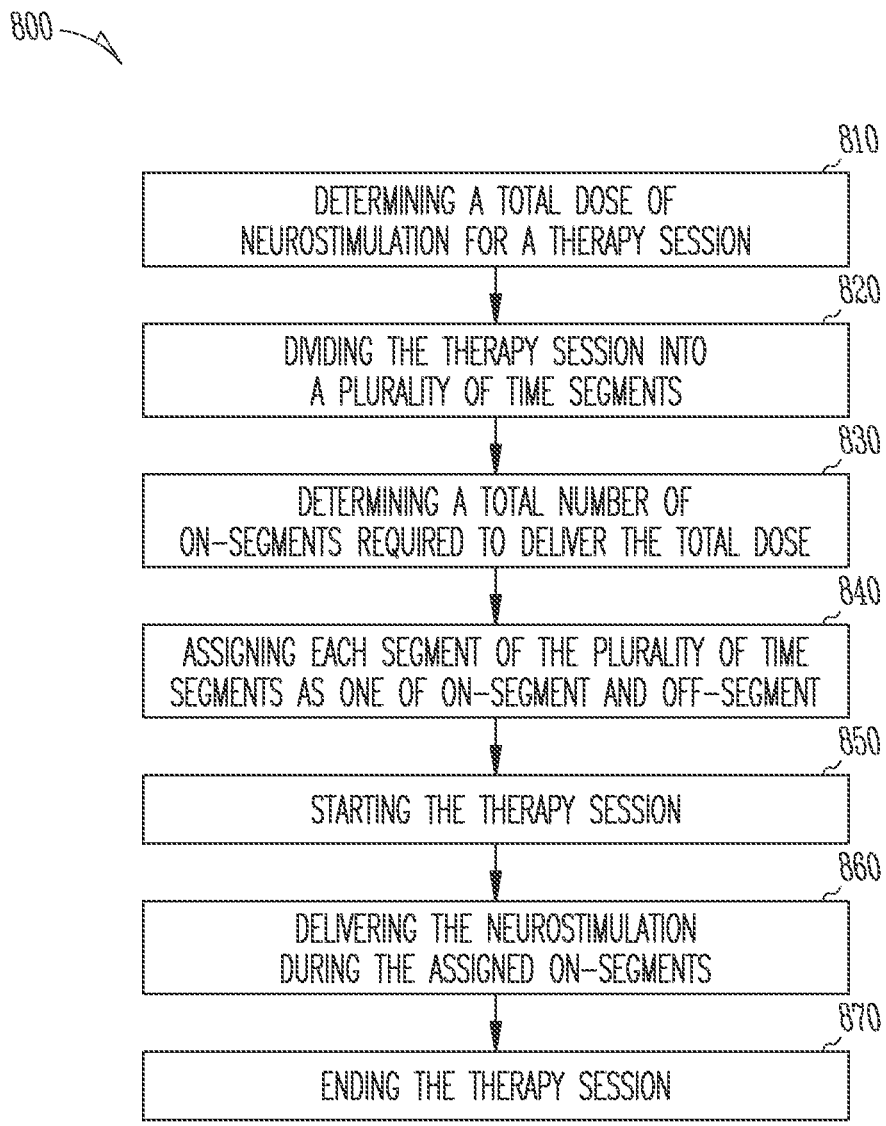
FIG. 8 is a flow chart illustrating an embodiment of a method for controlling neurostimulation for a specified total dose while preventing neural accommodation.

FIG. 8 is a flow chart illustrating an embodiment of a method 800 for controlling neurostimulation for a specified total dose while preventing neural accommodation. In one embodiment, method 800 is performed using system 100, including its various embodiments discussed in this document. In method 800, the neurostimulation is delivered for a specified dose for each therapy session. The therapy session has a session duration that is sufficiently long to allow the specified dose to be administrated intermittently. In one embodiment, the specified does is expressed as duration. When the neurostimulation is delivered as electrical pulses with a specified duration of the therapy session and a specified pulse frequency, the specified dose (as a duration) is a dosing parameter representative of the dose of the neurostimulation for the therapy session measured by the number of the electrical pulses delivered during the therapy session.

When the neurostimulation is to be delivered intermittently, the session duration may be divided into a plurality of on-segments and off-segments. The on-segment is a segment of time during which the neurostimulation is delivered. The off-segment is a segment of time during which the neurostimulation is not delivered. It is observed that within a limited range, the distribution of the on-segments and the off-segments does not substantially affect the efficacy of the neurostimulation as long as the specified dose is delivered during the on-segments. Therefore, in method 800, the one or more primary parameters include the specified dose, which is a measure of total dosing of the neurostimulation for a therapy session. The session duration is divided into a plurality of segments. In one embodiment in which the neurostimulation includes electrical pulses, the specified dose is a specified total stimulation duration over which the neurostimulation is delivered. The one or more secondary parameters include a segment duration parameter and an on-off parameter. The segment duration parameter specifies a segment duration being the duration of each segment of the plurality of segments. The on-off parameter specifies whether each segment of the plurality of segments is an on-segment or an off-segment.

At 810, a total dose of the neurostimulation for a therapy session is determined to be used as the specified dose. At 820, the therapy session is divided into a plurality of time segments. At 830, a total number of the on-segments required to deliver the total dose is determined. At 840, each segment of the plurality of time segments is assigned as one of the on-segment and the off-segment. In various embodiments, the segments are assigned on a random, pseudo-random, or other substantially aperiodic basis. In other words, the on-segments are distributed over the session duration in a random, pseudo-random, or other substantially aperiodic manner. At 850, the therapy session is started. At 860, the neurostimulation is delivered during the assigned on-segments. At 870, the therapy session ends, after the total dose has been delivered.

Various stimulation parameters used as the primary and secondary parameters are discussed in methods 600, 700, and 800, with reference to FIGS. 6-8, by way of example, but not by way of limitation. In methods 600, 700, and 800, the one or more parameters specify a measure of total dose of the neurostimulation for a therapy session. When the neurostimulation is delivered as electrical pulses with a specified duration of the therapy session and a specified pulse frequency, this measure of total dose of the neurostimulation is expressed as a duty cycle or a total stimulation duration and represents the total number of the electrical pulses delivered during the therapy session. In various embodiments, the one or more primary parameters include any parameter or combination of parameters identified to be useable for maintaining efficacy of neurostimulation, and the one or more secondary parameters include any parameter or combination of parameters identified to be useable for preventing neural accommodation without substantially affecting the efficacy of neurostimulation. In various embodiments, the one or more secondary parameters can be set to varying values without substantially changing the one or more values of the one or more primary parameters.

Figure 9:
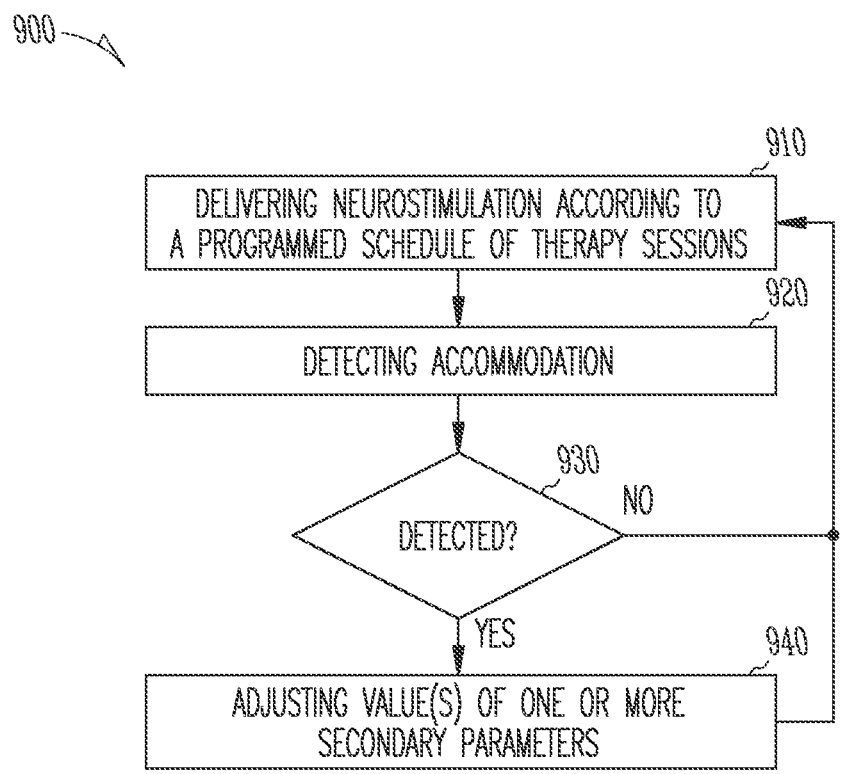
FIG. 9 is a flow chart illustrating an embodiment of a method for adjusting parameters in response to detection of neural accommodation.

FIG. 9 is a flow chart illustrating an embodiment of a method 900 for adjusting parameters in response to detection of neural accommodation. In one embodiment, method 900 is performed using system 100, including its various embodiments discussed in this document. In method 900, the one or more secondary parameters are adjusted only in response to detection of neural accommodation. That is, in response to the detection of neural accommodation, methods 600, 700, and/or 800 are performed. For example, secondary parameter adjuster 358 is enabled by the detection of neural accommodation.

At 910, the neurostimulation is delivered according to a programmed schedule of therapy sessions. At 920, neural accommodation is being detected. In response to a detection of neural accommodation at 930, the one or more values of the one or more secondary parameters are adjusted at 940. If neural accommodation is not detected at 930, the neural accommodation continues to be delivered, without adjusting the one or more secondary parameters.

Figure 10:
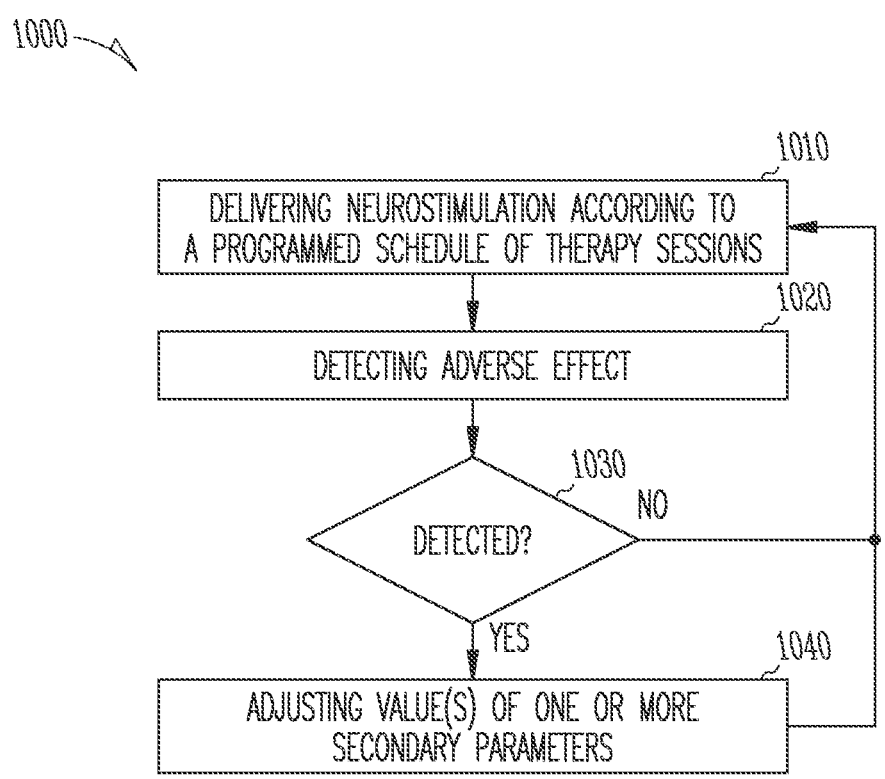
FIG. 10 is a flow chart illustrating an embodiment of a method for adjusting parameters in response to detection of an adverse effect.

FIG. 10 is a flow chart illustrating an embodiment of a method 1000 for adjusting parameters in response to detection of an adverse effect. In one embodiment, method 1000 is performed using system 100, including its various embodiments discussed in this document. In method 1000, the one or more secondary parameters are adjusted only in response to detection of an adverse effect. That is, in response to the detection of the adverse effect, methods 600, 700, and/or 800 are performed. For example, secondary parameter adjuster 358 is enabled by the detection of the adverse effect, This provides system 100 with a safety measure in case the one or more secondary parameters are set to one or more values that causes an unintended effect that may be harmful to the patient.

At 1010, the neurostimulation is delivered according to a programmed schedule of therapy sessions. At 1020, an adverse effect is being detected. In response to a detection of the adverse effect at 1030, the one or more values of the one or more secondary parameters are adjusted at 1040. If no adverse effect is detected at 1030, the neural accommodation continues to be delivered, without adjusting the one or more secondary parameters.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for delivering neurostimulation, comprising:
   a stimulation output circuit configured to deliver neurostimulation; and
   a control circuit configured to control the delivery of the neurostimulation using a plurality of stimulation parameters including one or more primary parameters each having a value selected for efficacy of the neurostimulation and one or more secondary parameters each having a value adjustable for preventing neural accommodation while maintaining the efficacy of the neurostimulation, the one or more primary parameters including a duty cycle being a ratio of an on-period to a sum of the on-period and an off-period, the on-period being a time period during which the neurostimulation is delivered, the off-period being a time period during which the neurostimulation is not delivered, the control circuit including a parameter adjuster configured to adjust the one or more secondary parameters without varying the one or more primary parameters including the duty cycle.

2. The system of claim 1, wherein the parameter adjuster is configured to adjust the on-period and the off-period without varying the duty cycle, the on-period and the off-period each being a parameter of the one or more secondary parameters.

3. The system of claim 1, wherein the parameter adjuster is configured to adjust a duration of a ramp during which a stimulation intensity gradually increases from zero to its value specified for the on-period when the ramp ends at a beginning of the on-period or gradually decreases from its value specified for the on-period to zero the ramp starting at an end of the on-period, the duration of the ramp being a parameter of the one or more secondary parameters.

4. The system of claim 1, wherein the parameter adjuster is configured to adjust the one or more secondary parameters for one or more values of the one or more secondary parameters to vary in a substantially aperiodic order.

5. The system of claim 4, wherein the parameter adjuster is configured to adjust the one or more secondary parameters for one or more values of the one or more secondary parameters to vary in a random or pseudo-random order.

6. The system of claim 1, further comprising:
   a sensing circuit configured to sense one or more physiological signals indicative of a degree of modulation of one or more physiological functions by the neurostimulation; and
   a neural accommodation detector configured to detect an indication of neural accommodation using the sensed one or more physiological signals,
   wherein the parameter adjuster is configured to adjust the one or more secondary parameters in response to a detection of the indication of neural accommodation.

7. The system of claim 6, wherein the neural accommodation detector is configured to detect a substantial decrease in the degree of modulation of the one or more physiological functions by the neurostimulation.

8. The system of claim 6, wherein the neural accommodation detector is configured to detect a substantial increase in a stimulation threshold being a minimum intensity of the neurostimulation that results in a detectable modulation of the one or more physiological functions in response to the neurostimulation.

9. A method for delivering neurostimulation, comprising:
   delivering the neurostimulation;
   controlling the delivery of the neurostimulation using a plurality of stimulation parameters including one or more primary parameters each having a value selected for efficacy of the neurostimulation and one or more secondary parameters each having a value adjustable for preventing neural accommodation while maintaining the efficacy of the neurostimulation, the one or more primary parameters including a duty cycle being a ratio of an on-period to a sum of the on-period and an off-period, the on-period being a time period during which the neurostimulation is delivered, the off-period being a time period during which the neurostimulation is not delivered; and
   adjusting the one or more secondary parameters without varying the one or more primary parameters including the duty cycle.

10. The method of claim 9, further comprising storing a plurality of value sets for the one or more secondary parameters, the value sets each including a value for each of the one or more secondary parameters, and wherein adjusting the one or more secondary parameters comprises changing one or more values of the one or more secondary parameters by selecting a value set from the stored plurality of value sets.

11. The method of claim 10, wherein selecting the value set from the stored plurality of value sets comprises selecting the value set in a random or pseudo-random order.

12. The method of claim 10, wherein storing the plurality of value sets for the one or more secondary parameters comprises generating a sequence of the value sets in a random or pseudo-random order of values and storing the generated sequence.

13. The method of claim 9, wherein the one or more secondary parameters comprise the on-period and the off-period.

14. The method of claim 9, wherein the one or more secondary parameters comprise a duration of a ramp during which a stimulation intensity gradually increases from zero to its value specified for the on-period when the ramp ends at a beginning of the on-period or gradually decreases from its value specified for the on-period to zero the ramp starting at an end of the on-period.

15. The method of claim 11, wherein adjusting the one or more secondary parameters comprises adjusting the one or more secondary parameters in response to an indication of neural accommodation.

16. The method of claim 15, further comprising:
sensing one or more physiological signals indicative of a degree of modulation of one or more physiological functions by the neurostimulation; and
detecting the indication of neural accommodation using the sensed one or more physiological signals.

17. A non-transitory computer-readable storage medium including instructions, which when executed by a system, cause the system to:
delivering the neurostimulation;
controlling the delivery of the neurostimulation using a plurality of stimulation parameters including one or more primary parameters each having a value selected for efficacy of the neurostimulation and one or more secondary parameters each having a value adjustable for preventing neural accommodation while maintaining the efficacy of the neurostimulation, the one or more primary parameters including a duty cycle being a ratio of an on-period to a sum of the on-period and an off-period, the on-period being a time period during which the neurostimulation is delivered, the off-period being a time period during which the neurostimulation is not delivered; and
adjusting the one or more secondary parameters without varying the one or more primary, parameters including the duty cycle.

18. The non-transitory computer-readable storage medium of claim 17, wherein the instructions, when executed by the system, cause the system to adjust the on-period and the off-period without varying the duty cycle, the on-period and the off-period each being one of the one or more secondary parameters.

19. The non-transitory computer-readable storage medium of claim 17, wherein the instructions, when executed by the system, cause the system to adjust a ramp duration without varying the duty cycle, the ramp duration being a duration of a ramp during which a stimulation intensity gradually increases from zero to its value specified for the on-period when the ramp ends at a beginning of the on-period or gradually decreases from its value specified for the on-period to zero the ramp starting at an end of the on-period.

20. The non-transitory computer-readable storage medium of claim 17, wherein the instructions, when executed by the system, cause the system to adjust the one or more secondary parameters in response to an indication of neural accommodation.

* * * * *